United States Patent
Suga

[11] Patent Number: 5,989,030
[45] Date of Patent: Nov. 23, 1999

[54] DENTAL IMPLANT

[76] Inventor: Shinichi Suga, 25-9 Fukasawa 5-chome, Setagaya-ku, Tokyo, Japan

[21] Appl. No.: 08/912,578

[22] Filed: Aug. 18, 1997

Related U.S. Application Data

[63] Continuation-in-part of application No. 08/582,543, Jan. 3, 1996, abandoned.

[51] Int. Cl.$^6$ .................................................... A61C 8/00
[52] U.S. Cl. ............................................................. 433/176
[58] Field of Search ................................... 433/172, 173, 433/176, 197, 198, 201.1

[56] References Cited

U.S. PATENT DOCUMENTS

| | | | |
|---|---|---|---|
| 2,449,522 | 9/1948 | White | 433/173 |
| 3,979,828 | 9/1976 | Taylor | 433/201.1 |
| 4,802,847 | 2/1989 | Komatsu | 433/176 |
| 5,006,070 | 4/1991 | Komatsu | 433/176 |
| 5,302,128 | 4/1994 | Suga | 433/176 |
| 5,370,695 | 12/1994 | Meuli et al. | 433/173 |

FOREIGN PATENT DOCUMENTS

| | | | |
|---|---|---|---|
| 2610819 | 8/1988 | France | 433/173 |
| 1203093 | 8/1970 | United Kingdom | 433/173 |

*Primary Examiner*—Ralph A. Lewis
*Attorney, Agent, or Firm*—Evenson, McKeown Edwards & Lenahan, PLLC

[57] ABSTRACT

A dental implant of which body has a form tapering toward its top and has a plurality of mountain-shaped projections emissively; said projections being cut off in its center, and ridge line portions of said projections which contact with compact bone portion of an alveolar bone at the time of insertion, being in a shape that said ridge lines increase its size upwardly; and a head for supporting an artificial tooth. The implant is useful for repairing lost canines.

1 Claim, 3 Drawing Sheets

DENTAL IMPLANT

This is a continuation-in-part of application Ser. No. 08/582,543, filed Jan. 3, 1996, abandoned.

BACKGROUND OF THE INVENTION

The present invention relates to a dental implant, and more particularly relates to an implant suitable for repairing lost canine teeth.

It is known that lost teeth can be repaired with artificial teeth which are mounted on artificial tooth roots, i.e. dental implants implanted in an alveolar bone.

Varieties of dental implants are proposed, and the present inventor has also proposed a very efficient blade-type implant, which has matured to U.S. Pat. No. 5,302,128.

The blade-type implant requires a long and narrow groove to be implanted in an alveolar bone, and is useful for repairing lost molar teeth, however, it is not suitable for repairing lost canines, because canines are located at the edge portion of the alveolar bone, and accordingly, the narrow and long groove which is capable of strongly supporting the implant cannot be dug.

A prior art implant suitable for repairing a lost canine has a structure provided with a rod-form body which should be implanted in an alveolar bone, and a pillar-form head which is mounted on the upper edge of the body and supports an artificial tooth.

In order to anchor the prior art implant, a hole which is adapted to receive the body is dug in the alveolar bone, an implant is inserted into the hole for an initial securing by a frictional connection, and after a certain period of time, the implant can be firmly secured with newly grown bone tissues of the alveolar bone.

The above known implant has the following disadvantages:

It is very difficult to form a hole in an alveolar bone, which should be completely fit to an implant to be embedded, because the practice is performed in the patient's mouth. When the size of the hole is too large for an implant, the embedded implant will wobble, and when the hole is too small, the implant cannot be inserted into the hole smoothly.

In the former case, the patient has to wait for a certain time period until the embedded implant is firmly secured by newly grown bone tissue, and in the latter case, the patient has to have repeated surgery until the hole becomes large enough to be adapted to receive an implant.

It is technically impossible to have a perfect phase contact between the outer peripheral of the rod form body and the inner peripheral of the hole, non-uniformity of the phase cannot be avoided, and cracks of the alveolar bone in the width direction have often been experienced, when the body is hammered to embed in the hole with a mallet.

Even when the implant adapts readily to the hole, the embedded implant is apt to move due to supersonic vibrations of the turbine for the dentist, and accordingly, dentists must avoid use of the turbine for treatment of teeth in the neighborhood of the implant.

In order to obtain stronger friction connection of the contact phase, the size of the hole is usually made as narrow as possible, and risks of cracks of the alveolar bone increase at the time of the insertion of the implant.

It is true that the contact phase between the implant and the hole is made larger, the friction connection force becomes stronger, however, an enlargement of the contact phase of the hole toward the periphery should be restricted by the next teeth, and its solution is directed to an enlargement of length to as deep as possible. Dentists have tried to make holes as deep as possible up to the neighborhood of mental foramen or lower alveolar vessel, and this surgery includes high risks.

Legs of the lower portion of the implant usually reach inside of soft sponge bone of the alveolar bone, the implant sinks unnecessarily deep if it is tapped into the hole with a mallet, and it also gradually sinks too much due to daily bites after the completion of surgery.

Furthermore, holes for inflow of blood into bone tissues which contact the implant body are provided with the body of the implant. However, the number of holes is limited to as few as possible in order to increase the contact phase between the outer periphery of the body and the inner periphery of the holes for the implant as large as possible. Accordingly, effective contact of bone with the body cannot be obtained in the event that growth of new bone tissue is insufficient for lack of necessary blood supply, or bone tissues are completely destroyed (necrosis) in the event that blood supply is not totally available.

As is explained above, dental implants include many clinical problems hard to solve and accordingly, have not been very popular yet.

In spite of the above disadvantages, the dental implant is fully acknowledged as useful, e.g., for supplemental support of long span bridges, and technological improvement has strongly been demanded in this field, especially from patients who have psychological aversions to artificial teeth.

BRIEF DESCRIPTION OF THE INVENTION

The present invention provides an improvement over the disadvantages of the prior art dental implants.

A dental implant comprising:

a body having a form tapering toward its top and having a plurality of mountain shape projections emissively;

said projections being cut off in the center, and ridge line portions of said projections which contact with compact bone portion of an alveolar bone at the time of insertion, being in a shape that said ridge lines increase its size upwardly; and a head for supporting an artificial tooth.

A dental implant of the present invention further comprising:

a number of said mountain-shaped projections of the body being five.

DETAILED DESCRIPTION OF THE INVENTION

Exemplary embodiments of the present invention are shown in FIGS. 1 through 5.

Figure 1:
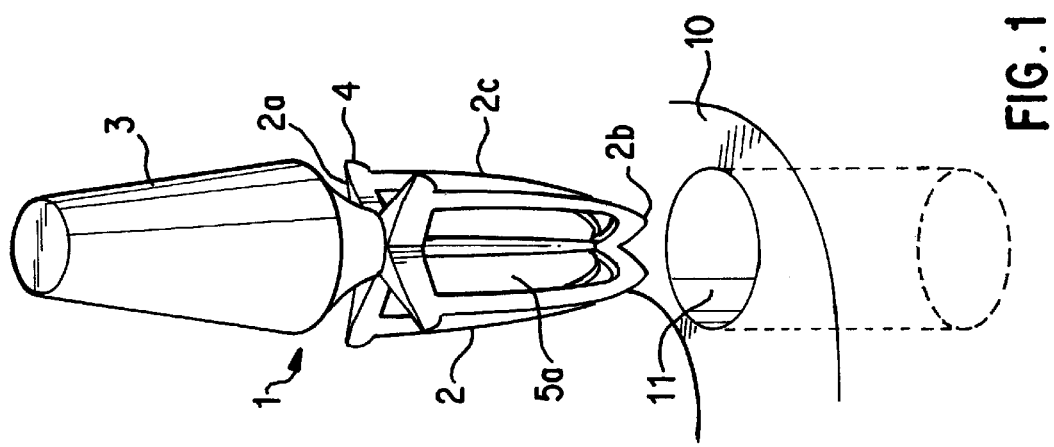
FIG. 1 is a perspective view of the dental implant of the present invention.

In FIG. 1, an implant 1 of the present invention is composed of a body 2 portion which should be inserted and imbedded in a hole 11 formed in an alveolar bone, and a head 3 portion which supports an artificial tooth (not shown).

Material of the implant of the present invention may be pure titanium, which has liophilic property, and which shows good and effective connection of the implant to the alveolar bone.

The body 2, which includes first and second end portions, has a shape tapering toward its second end portion or top and also has a plurality of mountain-shaped projections emissively in the direction of its diameter, namely in the shape of a star in its cross section.

Leg 2b at the first end portion or bottom edge of the body 2 is a sharp tip.

The number of the projections 2c has no limitation, however, may preferably be an odd number, and 5 projections made at 72 degree intervals may be useful in view of working convenience during the manufacturing process.

The center of the projection 2c is cut off to be a vacancy 5a.

Figure 2:
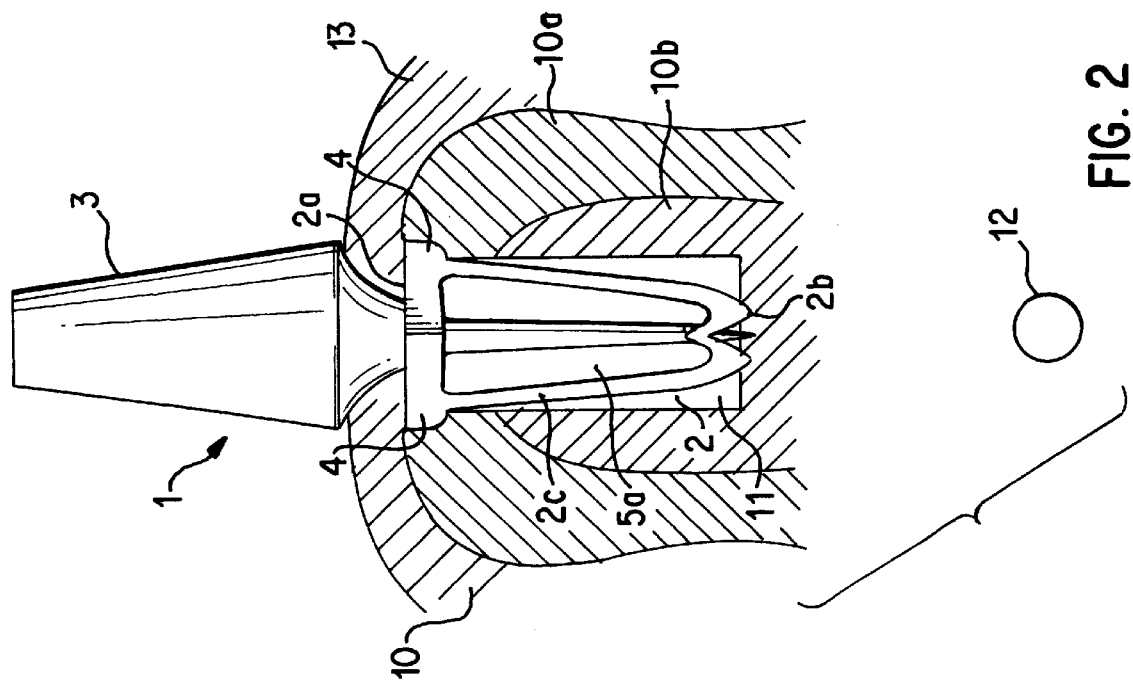
FIG. 2 is an elevational view of the dental implant as imbedded in an alveolar bone.
Figure 3:
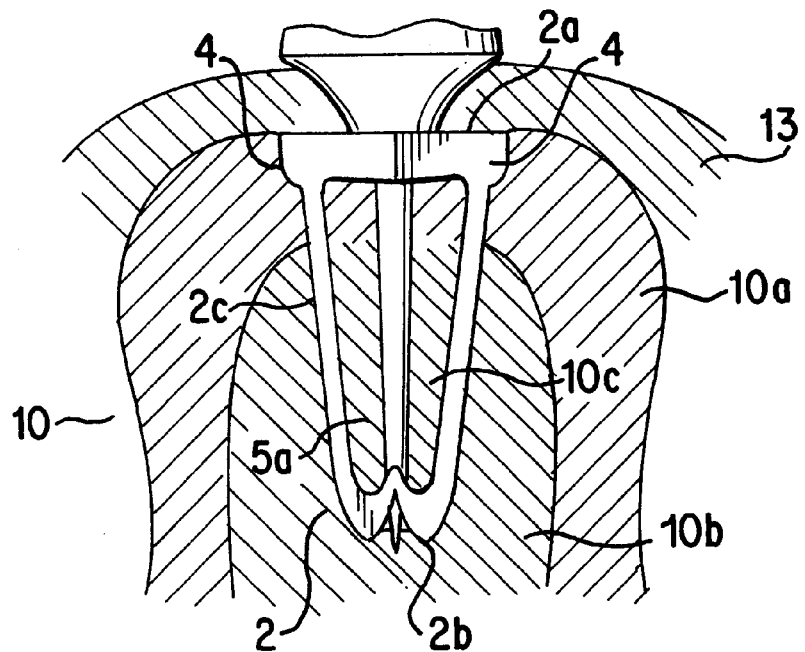
FIG. 3 is an enlarged elevational view of the dental implant as imbedded in the bone, where bone tissue has newly grown after insertion of the implant.
Figure 5:
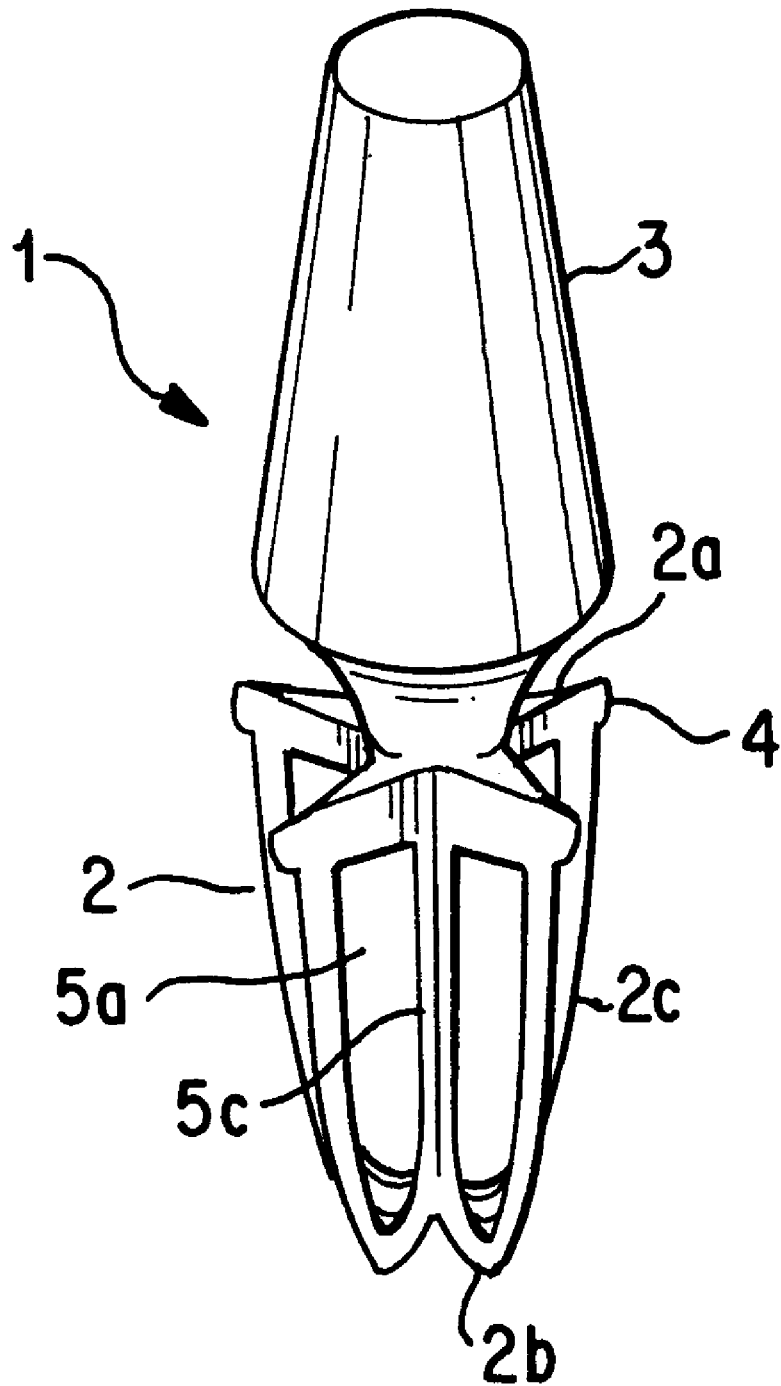
FIG. 5 is another perspective view of the dental implant of FIG. 1.

The center portion of the projection 2c may be thoroughly removed to make a vacancy 5a up to the starting portion of the projection 2c, as is shown in FIGS. 1 through 3 (to cut off even its axis of the body), or the axis may remain as an axis 5c, as shown in FIG. 5.

The top of the body is in a form of an overhang 4, of which the ridge line has a sharp form. The ridge line of the projection 2c increases its size tapering upwardly up to a neck shoulder 2a, as is shown in FIGS. 1 through 3.

The overhang 4 may be positioned within the compact bone 10a in the alveolar bone i.e, when embedded (usually 4–5 mm in width), as shown in FIG. 2.

In the embodiment, the body a height of about 12 mm, and the overhang has a height of about 2 mm.

Figure 4:
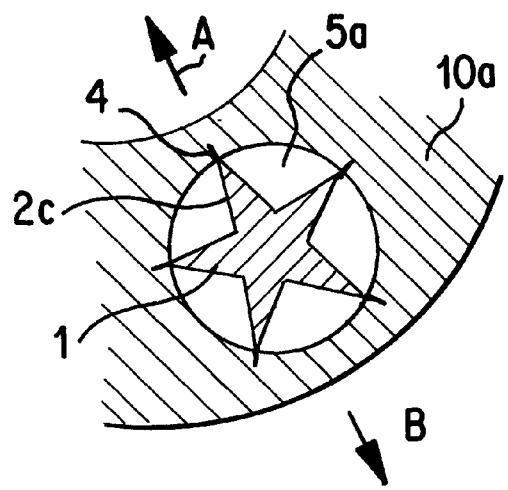
FIG. 4 is a cross-sectional view of the imbedded implant in a mouth.

The dental implant 1 of the present invention is inserted to imbed into a hole 11 prepared in an alveolar bone 10 for use (FIGS. 2 to 4).

In the Figures, numeral 10b is a sponge bone, 13 is gum, and 12 is alveolus vessel.

The dental implant of the present invention has a structure in which its body 2 has a form tapering toward its tip and has mountain-shaped projections 2c emissively in the direction of its diameter in the shape of a star in cross section, and accordingly it can be inserted smoothly into the hole 11.

The projection 2c of the body 2 having vacancy 5a has a flexibility toward the axial direction of the projection 2c, even if it is made of hard metal, and accordingly, even when the size of the hole 11 is rather small, the body can be inserted smoothly into the hole by using its flexibility without charging an excessive load onto the alveolar bone 10. The imbedded projection pushes back the hole toward its restoration direction, and accordingly, a strong friction connection between the implant and the hole can be obtained.

The top of the body 2 has an overhang 4, of which the ridge line is tapered to increase its size upwardly, the overhang bites the inner part of the hole 11 by hitting with a mallet, and the biting force prevents the implant from wobbling.

The ridge line of the overhang 4 is sharper, and a stronger biting force can be obtained.

The sharp tip of the leg 2b at the bottom of the body 2 also sinks into the bottom of the hole 11 and provides strong anchoring.

The overhang 4 is placed within the range of a compact bone 10a of the alveolar bone 10 and supported by a strong compact bone 10a, instead of by a soft sponge bone 10b as in the prior art implant technology, and unnecessary sinking of the implant can be prevented even with long-term biting pressure.

Furthermore, the following two efficient activities of the dental implant of the present invention give additional useful synergy effect of preventing the alveolar bone from cracking in the width direction. That is, (1) a plurality of the mountain-shaped projections contact an inner wall of the hole 11 uniformly at the ridge lines, and accordingly pushing force by the ridge line against the alveolar bone 10 is dispersed uniformly; (2) the tapering ridge lines of the overhang 4 increasing its height upwardly intrude firmly into the alveolar bone, and its load against the alveolar bone 10 in the width direction can be partly absorbed. The ridge line of the overhang is sharper, and the effect of the above (2) is stronger.

The vacancy 5a in the projection 2c gives an ample supply of blood to the entire bone tissues to grow, and newly grown bone 10c in the alveolar bone strong connection of the implant to the bone (see FIG. 3).

Stress of the implant when biting against the alveolar bone can be dispersed by placing the implant so that the number of projections 2c at the side of a cheek is larger than those at the side of a tongue, as is shown in FIG. 4.

By applying five extruded walls and overhanging portions, occurrence of a linear crack in the alveolar bone is prevented, and it then becomes possible to hammer the implant with confidence with a mallet or the like which was not previously used for fear of cracking of the alveolar bone towards its breadth.

What I claim is:

1. A method of implanting a dental implant into the jaw of a patient comprising:

providing a dental implant having a body with a first end portion comprising a head for receiving an artificial tooth and a second end portion at an opposite end to said first end portion, said body tapering outwardly from said second end portion to a lower end of said head and having an odd number of radially projecting blades connected to said lower end of said head, said radially projecting blades having openings therein and edges defining ridge lines for contacting a compact bone portion of an alveolar bone when inserted into the jaw, each ridge line terminating at a radially overhanging portion having a greater radial extent than each blade; and inserting the dental implant into a hole formed in the alveolar bone of the jaw so that a greater number of said radially projecting blades extend toward the patient's cheek than the patient's tongue and so that the overhanging portions of the radially extending blades are embedded in the compact bone portion of the alveolar bone.

* * * * *